(12) United States Patent
Guala

(10) Patent No.: US 6,843,513 B2
(45) Date of Patent: Jan. 18, 2005

(54) MALE LUER LOCK CONNECTOR FOR MEDICAL FLUID LINES

(75) Inventor: Gianni Guala, Turin (IT)

(73) Assignee: Industrie Borla S.p.A., Turin (IT)

( * ) Notice: Subject to any disclaimer, the term of this patent is extended or adjusted under 35 U.S.C. 154(b) by 59 days.

(21) Appl. No.: 10/396,568

(22) Filed: Mar. 26, 2003

(65) Prior Publication Data

US 2003/0184090 A1 Oct. 2, 2003

(30) Foreign Application Priority Data

Mar. 27, 2002 (IT) .................................. TO2002A00276

(51) Int. Cl.[7] ........................ F16L 25/00; A61M 25/18; A61M 39/10
(52) U.S. Cl. ........................ 285/332; 285/92; 604/533; 604/534; 604/535; 604/905
(58) Field of Search .................................. 285/332, 386, 285/81, 92, 93, 330, 332.1; 604/533, 534, 535

(56) References Cited

U.S. PATENT DOCUMENTS

| | | | | |
|---|---|---|---|---|
| 4,294,250 A | * | 10/1981 | Dennehey | .................. 604/403 |
| 4,296,949 A | * | 10/1981 | Muetterties et al. | .......... 285/18 |
| 4,452,473 A | * | 6/1984 | Ruschke | ...................... 285/81 |
| 4,639,019 A | * | 1/1987 | Mittleman | .................. 285/332 |
| 5,047,021 A | * | 9/1991 | Utterberg | ..................... 604/533 |
| 5,620,427 A | * | 4/1997 | Werschmidt et al. | ....... 604/535 |
| 5,651,776 A | * | 7/1997 | Appling et al. | ............. 604/534 |
| 5,702,374 A | * | 12/1997 | Johnson | ..................... 604/533 |
| 5,992,899 A | * | 11/1999 | Strowe | ......................... 285/93 |
| 6,083,194 A | * | 7/2000 | Lopez | .......................... 604/28 |
| 6,332,633 B1 | * | 12/2001 | Fitoussi et al. | ............. 285/332 |
| 6,638,256 B2 | * | 10/2003 | Jansen et al. | ............... 604/198 |

* cited by examiner

Primary Examiner—James M. Hewitt
(74) Attorney, Agent, or Firm—Sughrue Mion, PLLC

(57) ABSTRACT

A male luer lock connector for medical fluid lines comprising an elongated tubular body having an end portion with external luer cone and an internally threaded bushing mounted so that it can turn and slide on a portion with a cylindrical external surface of the tubular body. Cooperating formations disposed between the portion with cylindrical external surface of the tubular body and the bushing are provided to produce during use a perceptible click when the bushing draws near to a fully advanced position of engagement with a female luer lock connector.

11 Claims, 2 Drawing Sheets

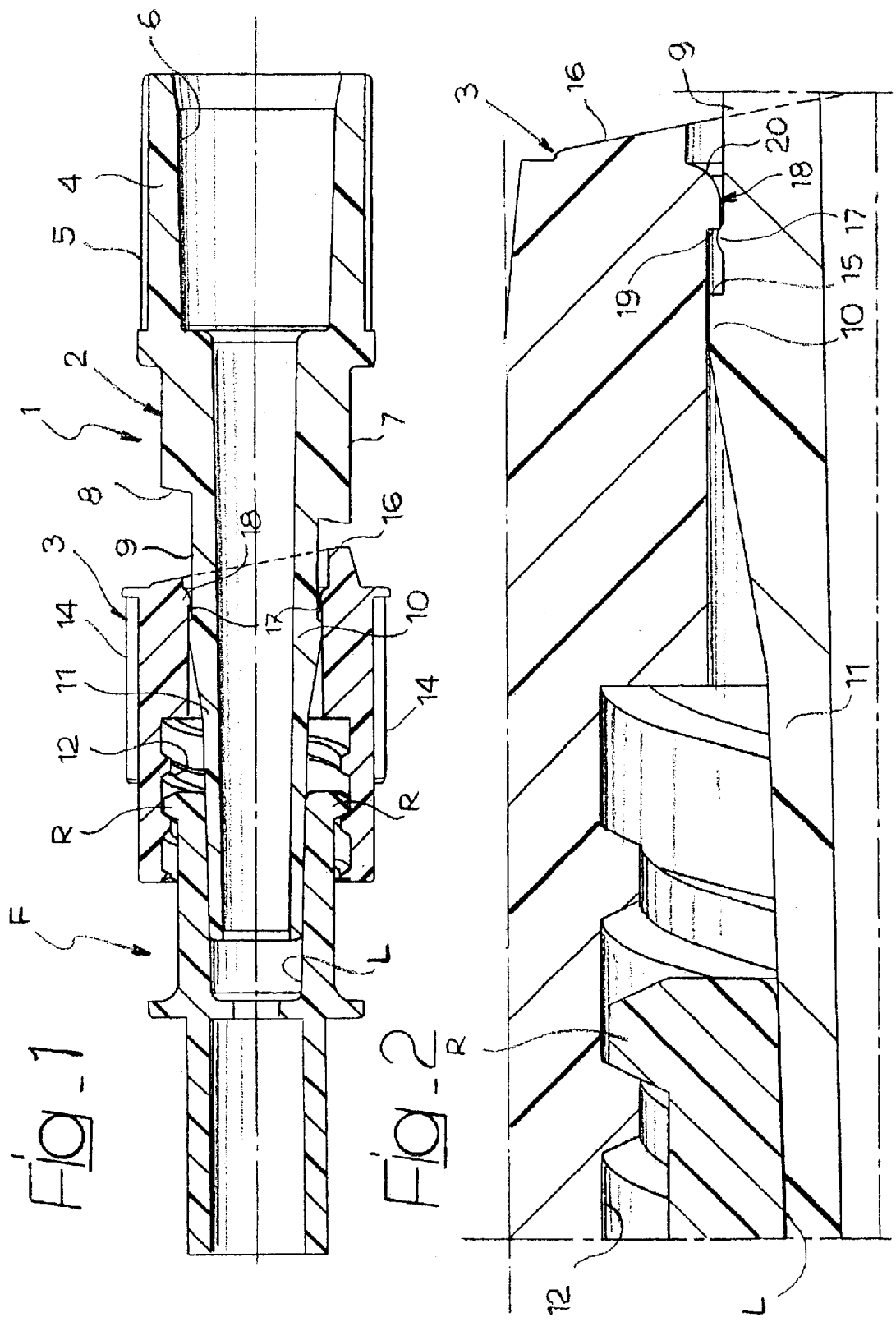

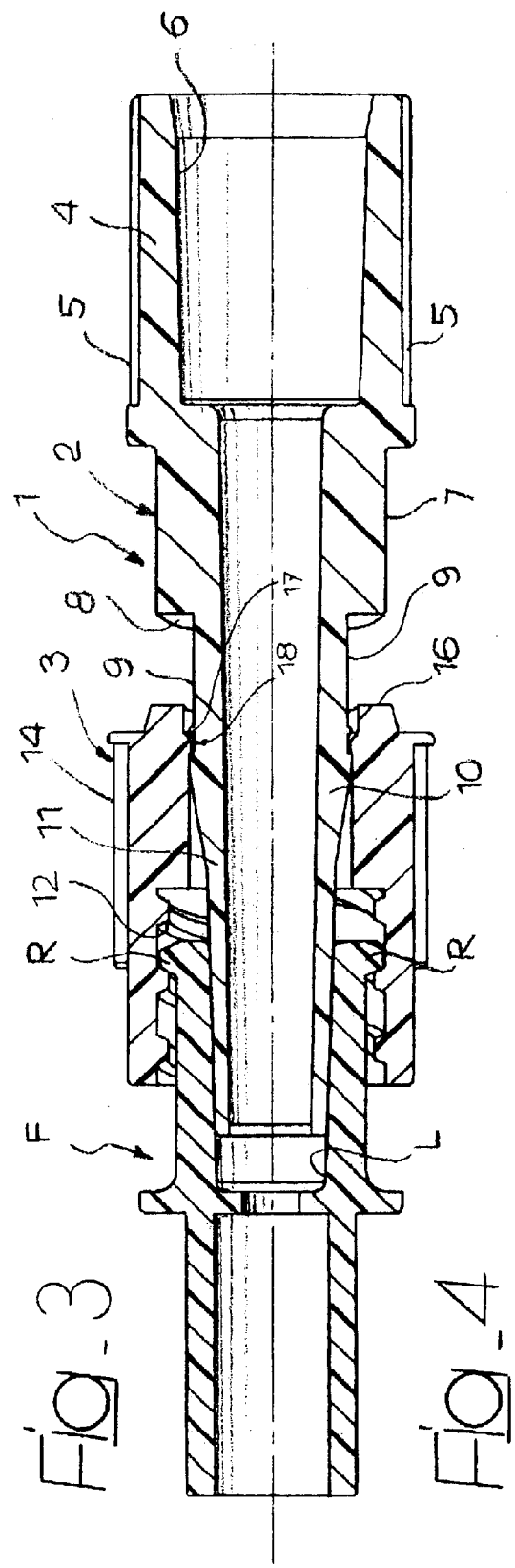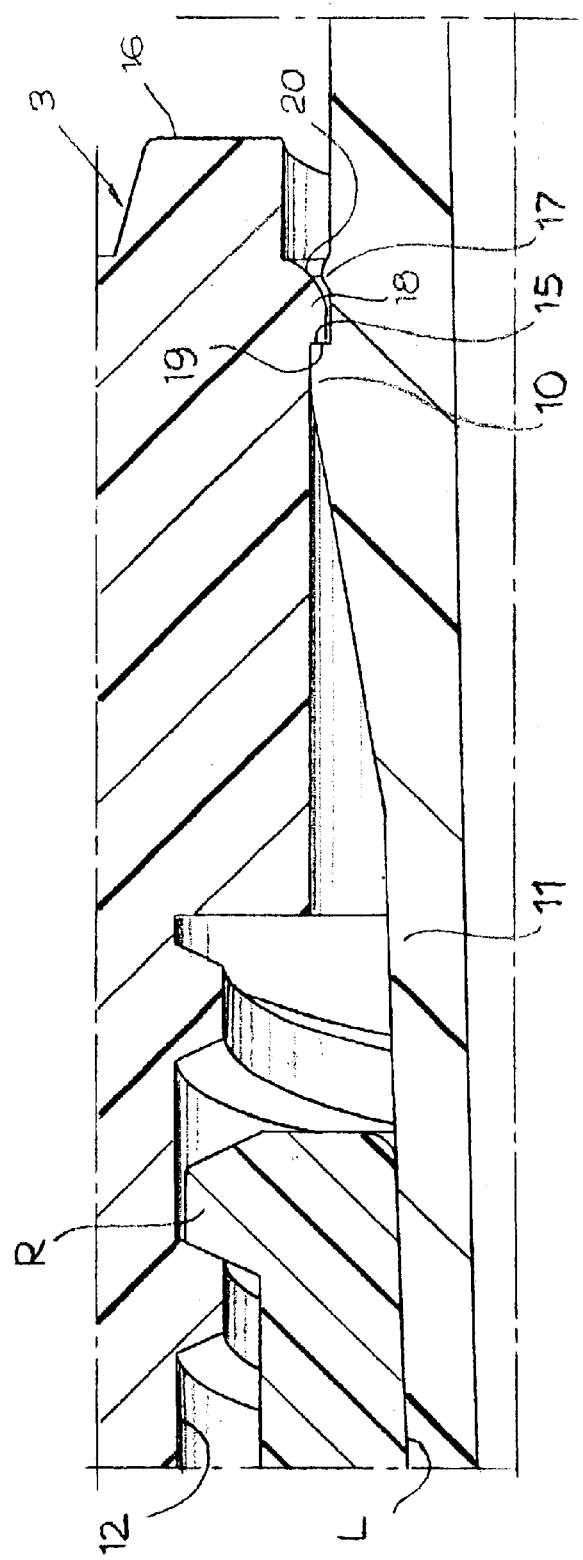

MALE LUER LOCK CONNECTOR FOR MEDICAL FLUID LINES

FIELD OF THE INVENTION

The present invention relates in general to connectors for medical fluid lines, and more specifically regards a male luer lock connector of the type comprising an elongated tubular body having a portion with a cylindrical external surface and an end portion with an external luer cone, and a bushing mounted on said portion with external cylindrical surface of the tubular body in such a way that it can turn and slide axially starting from a drawn-back position towards a fully advanced position, in which the bushing has an internal thread in which a female luer lock connector can be screwed, the end portion with external luer lock of the tubular body being designed to engage axially with the female luer lock connector.

STATE OF THE PRIOR ART

In a first known type of luer lock connector of the type defined above the axial travel of the bushing has a length that consents engagement of the end portion with external luer cone of the body of the male connector inside the female connector without having to even partially screw the internal thread of the bushing screwed on the female luer lock connector. This arrangement offers a certain degree of safety during use, as the connection between the male connector and the female connector is to a certain extent guaranteed even following simple axial engagement between the respective luer cones, that is even if the bushing of the male connector is not screwed fully down on the female connector due to inattentiveness or inexperience of the operator. In this situation, there is in any case a risk of accidental separation between the male connector and the female connector, with the critical consequences that could arise for the patient to which the connector is applied. Moreover, this arrangement has the drawback that disengagement and voluntary separation between the male connector and the female connector requires, after unscrewing the bushing, a certain degree of manual force for reciprocal axial removal of the respective luer cones, which may be difficult and awkward.

In a second type of known connector of the type specified above the axial travel of the bushing along the portion with cylindrical external surface of the tubular body of the male connector is reduced so as to prevent firm engagement of the end portion with external luer cone of the male connector in the female luer lock connector without at least partially screwing the internal thread of the bushing on the female connector. In this arrangement the portion with cylindrical external surface has an annular frontal reaction part which the bushing is designed to axially contrast in its drawn-back position to produce during use, after unscrewing the bushing in relation to the female luer lock connector, axial expulsion of said female luer lock connector from the end portion with external luer cone of the tubular body of the male connector. In practice, this produces an effect of self-separation between the male connector and the female connector when the bushing is further unscrewed to its drawn-back position, hence facilitating the operation to separate the male connector in relation to the female connector. This advantage is nonetheless offset by the drawback that unskilled, inattentive or negligent operators may make the connection between the male connector and the female connector without screwing, or without fully screwing down, the bushing, and therefore in a slack and unstable manner, with the danger of accidental separation between the two connectors and serious consequences for the patient to which the medical line is applied.

In a third type of connector of the type defined above, forming the object of the Italian patent application IT-A-TO2002A111 in the name of the Applicant, not published at the date of filing the present application, the axial travel of the bushing allows, in the drawn-back position of the bushing, engagement of the end portion with external luer cone of the body of the male connector in the female luer lock connector without even partially screwing said internal thread of said bushing on said female luer lock connector, and the reaction part of the portion with cylindrical external surface is generally formed of a cam surface so that the bushing in said drawn-back position can be positioned in at least a partially advanced condition to produce during use axial expulsion of said female luer lock connector.

This arrangement, which makes it possible to attain the advantages of the known connectors of the first and second type described above, is nonetheless still unable to guarantee total safety against the risks of accidental separation between the male luer lock connector and the female luer lock connector in the case in which, during use, the bushing of the former is not screwed fully down on the latter. Although remote, there is still a risk that in this case the medical line could open accidentally, with possible serious consequences for the patient to which it is applied.

To attempt to solve this problem the U.S. Pat. No. 5,620,427 proposes that the portion with cylindrical external surface of the tubular body and the bushing should be formed with substantially tapered reciprocally engaging surfaces designed to produce gradual frictional engagement between the two parts when the bushing draws near to the fully advanced position. The U.S. Pat. No. 4,294,250 also proposes providing the male connector and the female connector with visual indicating means designed to indicate the condition of correct connection.

These systems have nonetheless proved to be inadequate and in any case unable to guarantee a sufficiently high degree of safety.

SUMMARY OF THE INVENTION

The object of the present invention is to obviate this drawback, and to produce a male luer lock connector of the type defined above provided with an appreciably greater degree of safety against the risk of incomplete connection and in any case the risk of accidental separation of the male luer lock connector from the female luer lock connector.

According to the invention this object is attained substantially thanks to the fact that the connector comprises cooperating formations provided between the portion with cylindrical external surface of the tubular body and the bushing and designed to produce in use a click when said bushing, during axial travel of advance, draws near to said fully advanced position.

These formations are conveniently capable of producing a perceptible audible and/or tactile signal for the operator.

Thanks to this idea of solution, during use the connector according to the invention provides the operation with a clear and unequivocal signal of the fact that the male connector has been correctly connected to the female connector. In the absence of this signal, even an inexperienced or inattentive operator will immediately realize that in order to complete the connection securely he/she must rotate the bushing further in the direction of screwing, until perceiving the audible/tactile signal.

According to another characteristic of the invention, the aforesaid formations are mutually disengageable only after applying a positive unscrewing rotation to said bushing.

In this way disconnection of the male luer lock connector from the female luer lock connector may only be performed voluntarily, by manually unscrewing the bushing, which eliminates any risk of involuntary disengagement and hence of accidental aperture of the medical line.

BRIEF DESCRIPTION OF THE DRAWINGS

The invention shall now be described in detail with reference to the accompanying drawings, provided purely as a non-limiting example, in which:

FIG. 1 is a schematic longitudinal sectional view showing the male luer lock connector according to the invention represented in a first phase of connection to the female luer lock connector, FIG. 2 shows a part of FIG. 1 on a larger scale, FIG. 3 is an analogous view to FIG. 1 showing the male connector in a second phase of connection to the female connector, FIG. 4 shows a part of FIG. 3 on a larger scale.

DETAILED DESCRIPTION OF THE INVENTION

Firstly with reference to FIG. 1, the numeral 1 indicates generically a male luer lock connector according to the invention for medical fluid lines, for example for haemodialysis.

The male luer lock connector 1 is formed of two components, both of moulded plastic material: an elongated tubular body 2 and an internally threaded bushing 3.

The elongated tubular body 2 includes, in a single piece, an initial manoeuvring part 4 provided with longitudinal gripping projections 5 and the cavity of which, indicated with 6, is predisposed for connection of the end of a flexible tube not shown in the drawings. The manoeuvring part 4 is followed by a cylindrical intermediate part 7 in turn joined, through an annular frontal reaction part indicated with 8, to a portion with a cylindrical surface 9 of smaller diameter. The portion with cylindrical external surface 9 connects, through a slightly widened portion 10, to an end portion with external luer cone 11.

The cylindrical intermediate part 7 can be omitted, and in this case the annular frontal reaction part 8 will coincide with the edge of the manoeuvring part 4 facing the end portion with external luer cone 11.

The bushing 3 has an internal thread 12 and, externally, a series of axial manoeuvring projections 14. This bushing 3 is mounted on the portion with cylindrical external surface 9 of the tubular body 2 in such a way that it can both turn and axially slide for a travel of axial advance of a definite length starting from a drawn-back position (not shown in the drawings) defined by the axial arrest between the bushing 3 and the annular frontal reaction part 8 of the tubular body 2. The extent of axial advance of the bushing 3 corresponds to the length of the portion with cylindrical external surface 9 between the annular frontal reaction part 8 and the widened portion 10, which defines with said portion with cylindrical internal surface 9 an annular arrest shoulder 15.

In the case of the example shown the annular reaction part 8 consists of a bevelled inclined flat surface, defining as will be shown a thrust cam, cooperating with which is a corresponding bevelled flat back surface 16 of the end of the bushing 3 facing said surface 8.

According to a variant not shown (and described in the aforesaid Italian patent application IT-A-T02002A1111), the annular frontal reaction part 8 may be formed of a cam surface with rising/falling travel, cooperating with cam-follower projections formed at the back end of the bushing 3.

The extent of the axial travel of the bushing 3 along the cylindrical surface 9 between the drawn-back position, in which the surfaces 8 and 16 are in contact with each other, and a fully advanced position defined by annular arrest 15, is connected to the manner of engagement of the male luer lock connector 1 with a complementary female luer lock connector, indicated as a whole with F in the drawings.

This female luer lock connector F comprises, in the usual manner, a tubular body of moulded plastic material predisposed for example (although not necessarily) for the connection of a flexible tube, and an internal luer cone L, complementary to the end portion with external luer cone 11 of the male luer lock connector 1. The internal luer cone L is formed at its free end with external radial projections R which can engage with the thread 12 of the bushing 3. The projections R may be replaced by an external thread.

According to the fundamental characteristic of the invention, the portion with cylindrical external surface 9 of the tubular body 2 and the bushing 3 are provided with cooperating formations designed to produce, during use, a click which produces a perceptible audible and— secondarily—also tactile signal when the bushing 3, during its travel of advance, draws near to the fully advanced position.

These formations are composed of a series (at least two) of radial projections 17 formed on the cylindrical surface 9 at a short distance from the stop 15, and an annular ribbing 18 formed on the internal surface of the bushing 3 near to its back end 16.

The radial projections 17 have, in the example shown, a rounded profile, while the annular ribbing 18 has an axial frontal surface with a radial step 19 and a rounded axial back surface 20.

During operation, when the bushing 3 is in its fully drawn-back position, with the back end adjacent to the frontal reaction surface 8, the end portion with external luer cone 11 projects beyond the bushing 3 for a length which, as has been said, allows it to engage with interference inside the internal luer cone L of the female connector F without requiring to even partially screw the internal thread 12 of the bushing 3 on the projections R.

Starting from this position, engagement by screwing the internal thread 12 of the bushing 3 on the projections R of the female connector F produces further axial force of the external luer cone 10 in the internal luer cone L, to the position represented in FIGS. 1 and 2 in which the internal ribbing 19 of the bushing 3 reaches the radial projections 17 of the portion with cylindrical external surface 9. In this position, further screwing rotation of the bushing 3 causes the annular ribbing 18 to be exceeded by force, with a click effect which produces a perceptible, tactile and, above all, audible signal. This signal informs the operator in a direct and evident manner that the male connector 1 and the female connector F are joined together in a sufficiently secure manner against the effects of the risk of possible reciprocal accidental separation.

After the annular ribbing 18 has exceeded the radial projections 17, further screwing rotation of the bushing 3 produces definitive forced clamping between the male 1 and female F connectors corresponding to arrest of the stepped axial frontal surface 19 of the annular ribbing 18 against the annular arrest flange 15, in the manner shown in FIGS. 3 and 4. This final screwing phase of the bushing 3 may include a friction effect which may be obtained both by adjusting the configuration of the annular ribbing 18, limiting the radial clearance in relation to the projections 17, and by resorting to auxiliary devices such as the presence of axial splines (not shown in the drawings) on the cylindrical external surface 9 of the tubular body 2.

In the fully screwed condition of the bushing 3 shown in FIGS. 3 and 4, engagement of the male luer lock connector in relation to the female luer lock connector F is stably and securely guaranteed, guaranteeing the maximum degree of safety against risks of accidental disconnection caused by any movements, knocks, thermal dilation, etc. In fact, to produce disconnection between the two connectors 1 and F it is necessary to apply a positive unscrewing torque to the bushing 3 in order to allow the axial back surface 20 of the annular ribbing 18 to exceed the projections 17 so as to draw back the bushing 3. This is exceeded by friction, thanks to the rounded conformation of the axial back surface 20.

The bushing 3 may therefore be fully unscrewed so that its back end 16 is disposed against the frontal reaction surface 8. Starting from this position, further unscrewing rotation of the bushing 3 produces, following axial reaction between the surfaces 16 and 8 and interaction between the end part of the internal thread 12 and the projections R, an effect of extraction consisting in an axial thrust of the female connector F towards the outside of the male connector 1. This produces practical and easy disengagement of the external luer cone 11 from the internal luer cone L, with an action of expulsion of the latter.

It appears evident from the above that the male luer lock connector according to the invention is able to guarantee, compared with known connectors of the same type, much greater safety against risks both of incomplete or in any case insufficient connection to the female connector, and of involuntary or accidental separation between the two connectors. Added to these advantages are more practical and easier voluntary disconnection of the male connector from the female connector, with minimum manual force.

This effect is nonetheless optional, as the idea of solution consisting in providing a perceptible audible and possibly tactile signal during screwing of the bushing 3 may also be proposed in relation to luer lock connectors of a different type to the one described and illustrated, and in particular to connectors without the axial expulsion system of the female connector following unscrewing of the bushing 3.

Naturally, the constructional details and embodiments may vary widely from those described and illustrated, without however departing from the scope of the present invention as defined in the claims below.

What is claimed is:

1. A male luer lock connector for medical fluid lines comprising an elongated tubular body having a portion with a cylindrical external surface and an end portion with an external luer cone, and a bushing mounted on said cylindrical external surface of said tubular body so that it can turn and slide axially starting from a drawn-back position towards a fully advanced position, said bushing having an internal thread in which a female luer lock connector can be screwed, said end portion with said external luer cone of said tubular body being designed to engage axially with said female luer lock connector, further comprising cooperating formations provided between said portion with said cylindrical external surface of said tubular body and said bushing and designed to produce in use a click when said bushing, during axial travel of advance, draws near to said fully advanced position;

wherein said cooperating formations include radial projections on one of said portions with said cylindrical external surface or said tubular body of said bushing, and an annular ribbing on the other of said bushing or portion with said cylindrical external surface of said tubular body, respectively and wherein said annular ribbing has a stepped axial front surface and a rounded axial back surface.

2. Connector according to claim 1, wherein said click produces a perceptible audible signal.

3. Connector according to claim 1, wherein said formations are mutually disengageable only after applying a positive unscrewing rotation of said bushing.

4. Connector according to claim 3, wherein said cooperating formations are reciprocally disengageable with friction.

5. Connector according to claim 1, wherein said radial projections have a rounded profile.

6. Connector according to claim 1, wherein said cooperating formations are designed to also produce reciprocal frictional engagement following said click.

7. Connector according to claim 1, wherein said portion with said cylindrical external surface is formed of a frontal arrest part for said bushing in said fully advanced position.

8. Connector according to claim 1, wherein said portion with said cylindrical external surface has an annular reaction part which the bushing is designed to axially contract in said drawn-back position to produce during use, after unscrewing said bushing relative to said female luer lock connector, axial expulsion of said female luer lock connector from said end portion with said external luer cone of said tubular body.

9. Connector according to claim 1, wherein said bushing can slide axially along said portion with said cylindrical external surface of said tubular body for an axial travel of a length which allows, in said drawn-back position of said bushing, substantial and firm engagement of said end portion with said external luer cone in said female luer lock connector without even partially screwing said internal thread of said bushing on said female luer lock connector.

10. Connector according to claim 2, wherein said click also produces a perceptible tactile signal.

11. Luer lock connection assembly for medical fluid lines comprising a female luer lock connector and a male luer lock connector according to claim 1.

* * * * *